United States Patent
Ding (10) Patent No.: US 10,646,267 B2
(45) Date of Patent: May 12, 2020

(54) SURGICAL FORCEPS

(71) Applicant: COVIDIEN LP, Mansfield, MA (US)

(72) Inventor: Weijiang Ding, Shanghai (CN)

(73) Assignee: Covidien LLP, Mansfield, MA (US)

( * ) Notice: Subject to any disclaimer, the term of this patent is extended or adjusted under 35 U.S.C. 154(b) by 975 days.

(21) Appl. No.: 14/904,867

(22) PCT Filed: Aug. 7, 2013

(86) PCT No.: PCT/CN2013/080948
§ 371 (c)(1),
(2) Date: Jan. 13, 2016

(87) PCT Pub. No.: WO2015/017992
PCT Pub. Date: Feb. 12, 2015

(65) Prior Publication Data
US 2016/0157921 A1 Jun. 9, 2016

(51) Int. Cl.
*A61B 18/14* (2006.01)
*A61B 17/28* (2006.01)
(Continued)

(52) U.S. Cl.
CPC ...... *A61B 18/1442* (2013.01); *A61B 17/2816* (2013.01); *A61B 18/1445* (2013.01);
(Continued)

(58) Field of Classification Search
CPC ............ A61B 18/1442; A61B 18/1445; A61B 17/2812; A61B 17/2816; E05D 11/10; E05D 11/105; E05D 11/081; E05D 11/082

See application file for complete search history.

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| CA | 2104423 A1 | 2/1994 |
| DE | 2415263 A1 | 10/1975 |

(Continued)

OTHER PUBLICATIONS

Sigel et al., The Mechanism of Blood Vessel Closure by High Frequency Electrocoagulation, Surgery Gynecology & Dbstetrics, Oct. 1965 pp. 823-831.

(Continued)

*Primary Examiner* — Michael F Peffley
*Assistant Examiner* — Bo Ouyang
(74) *Attorney, Agent, or Firm* — Carter, DeLuca & Farrell LLP (57) ABSTRACT

An end effector assembly includes first and second jaw members pivotable between spaced-apart and approximated positions. The first and second jaw members include first and second proximal flanges, respectively. A pivot pin couples the proximal flanges of the jaw members to one another. The pivot pin includes a body and a head. The body is coupled to the first proximal flange. The head defines a first ramped surface configured to slidably contact a second ramped surface of the second proximal flange. In the spaced-apart position of the jaw members, the first and second ramped surfaces are oppositely disposed such that a maximum clearance is defined between the first and second proximal flanges. In the approximated position of the jaw members, the first and second ramped surfaces are similarly disposed such that a minimum clearance is defined between the first and second proximal flanges.

20 Claims, 5 Drawing Sheets

(51) Int. Cl.
    *A61B 17/29*        (2006.01)
    *A61B 18/00*        (2006.01)
(52) U.S. Cl.
    CPC ........... *A61B 2017/2947* (2013.01); *A61B 2018/0063* (2013.01); *A61B 2018/00601* (2013.01); *A61B 2018/1455* (2013.01)

(56) References Cited

U.S. PATENT DOCUMENTS

| | | |
|---|---|---|
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 2,002,594 A | 5/1935 | Wappler et al. |
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,279,753 A | 4/1942 | Knopp |
| 2,305,156 A | 12/1942 | Grubel |
| 2,327,353 A | 8/1943 | Karle |
| 2,632,661 A | 3/1953 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,913,586 A | 10/1975 | Baumgarten |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| 4,715,122 A | 12/1987 | Linden |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Kamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Shame et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Heidmueller et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |

(56) References Cited

U.S. PATENT DOCUMENTS

| | | |
|---|---|---|
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Faille et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,140 A | 10/1995 | Linden et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,591,202 A | 1/1997 | Slater et al. |
| 5,597,107 A | 1/1997 | Knodel et al. |
| 5,599,350 A | 2/1997 | Schulze et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossein et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins |
| 5,752,973 A | 5/1998 | Kieturakis |

(56) References Cited

U.S. PATENT DOCUMENTS

| | | |
|---|---|---|
| 5,755,717 A | 5/1998 | Yates et al. |
| 5,759,188 A | 6/1998 | Yoon |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,779,646 A | 7/1998 | Koblish et al. |
| 5,779,701 A | 7/1998 | McBrayer et al. |
| H1745 H | 8/1998 | Paraschac |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,093 A | 10/1998 | Williamson, IV et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,833,690 A | 11/1998 | Yates et al. |
| 5,843,080 A | 12/1998 | Fleenor et al. |
| 5,849,022 A | 12/1998 | Sakashita et al. |
| 5,853,412 A | 12/1998 | Mayenberger |
| 5,859,527 A | 1/1999 | Cook |
| 5,860,976 A | 1/1999 | Billings et al. |
| 5,876,401 A | 3/1999 | Schulze et al. |
| 5,876,412 A | 3/1999 | Piraka |
| 5,882,567 A | 3/1999 | Cavallaro et al. |
| 5,891,141 A | 4/1999 | Rydell |
| 5,891,142 A | 4/1999 | Eggers et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar et al. |
| 5,928,136 A | 7/1999 | Barry |
| 5,935,126 A | 8/1999 | Riza |
| 5,941,869 A | 8/1999 | Patterson et al. |
| 5,944,718 A | 8/1999 | Austin et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,004,335 A | 12/1999 | Vaitekunas et al. |
| 6,010,516 A | 1/2000 | Hulka |
| 6,017,358 A | 1/2000 | Yoon et al. |
| 6,021,693 A | 2/2000 | Feng-Sing |
| 6,024,741 A | 2/2000 | Williamson, IV et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,060,695 A | 5/2000 | Harle et al. |
| 6,066,139 A | 5/2000 | Ryan et al. |
| 6,074,386 A | 6/2000 | Goble et al. |
| 6,077,287 A | 6/2000 | Taylor et al. |
| 6,080,180 A | 6/2000 | Yoon et al. |
| RE36,795 E | 7/2000 | Rydell |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,096,031 A | 8/2000 | Mitchell et al. |
| 6,096,037 A | 8/2000 | Mulier et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,162,220 A | 12/2000 | Nezhat |
| 6,171,316 B1 | 1/2001 | Kovac et al. |
| 6,174,309 B1 | 1/2001 | Wrublewski et al. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,400 B1 | 2/2001 | Van De Moer et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |

(56) References Cited

U.S. PATENT DOCUMENTS

| | | | |
|---|---|---|---|
| 6,228,083 | B1 | 5/2001 | Lands et al. |
| 6,248,124 | B1 | 6/2001 | Pedros et al. |
| 6,248,944 | B1 | 6/2001 | Ito |
| 6,261,307 | B1 | 7/2001 | Yoon et al. |
| 6,267,761 | B1 | 7/2001 | Ryan |
| 6,270,497 | B1 | 8/2001 | Sekino et al. |
| 6,270,508 | B1 | 8/2001 | Klieman et al. |
| 6,273,887 | B1 | 8/2001 | Yamauchi et al. |
| 6,277,117 | B1 | 8/2001 | Tetzlaff et al. |
| 6,280,458 | B1 | 8/2001 | Boche et al. |
| 6,283,961 | B1 | 9/2001 | Underwood et al. |
| D449,886 | S | 10/2001 | Tetzlaff et al. |
| 6,298,550 | B1 | 10/2001 | Kirwan, Jr. |
| 6,302,424 | B1 | 10/2001 | Gisinger et al. |
| 6,312,430 | B1 | 11/2001 | Wilson et al. |
| 6,319,262 | B1 | 11/2001 | Bates et al. |
| 6,319,451 | B1 | 11/2001 | Brune |
| 6,322,561 | B1 | 11/2001 | Eggers et al. |
| 6,322,580 | B1 | 11/2001 | Kanner |
| 6,325,795 | B1 | 12/2001 | Lindemann et al. |
| 6,334,860 | B1 | 1/2002 | Dorn |
| 6,334,861 | B1 | 1/2002 | Chandler et al. |
| 6,345,532 | B1 | 2/2002 | Coudray et al. |
| 6,350,264 | B1 | 2/2002 | Hooven |
| 6,352,536 | B1 | 3/2002 | Buysse et al. |
| 6,358,249 | B1 | 3/2002 | Chen et al. |
| 6,358,259 | B1 | 3/2002 | Swain et al. |
| 6,358,268 | B1 | 3/2002 | Hunt et al. |
| 6,364,879 | B1 | 4/2002 | Chen et al. |
| D457,958 | S | 5/2002 | Dycus et al. |
| D457,959 | S | 5/2002 | Tetzlaff et al. |
| 6,387,094 | B1 | 5/2002 | Eitenmuller |
| 6,391,035 | B1 | 5/2002 | Appleby et al. |
| 6,398,779 | B1 | 6/2002 | Buysse et al. |
| 6,402,747 | B1 | 6/2002 | Lindemann et al. |
| 6,409,728 | B1 | 6/2002 | Ehr et al. |
| H2037 | H | 7/2002 | Yates et al. |
| 6,419,675 | B1 | 7/2002 | Gallo, Sr. |
| 6,425,896 | B1 | 7/2002 | Baltschun et al. |
| 6,432,112 | B2 | 8/2002 | Brock et al. |
| 6,440,144 | B1 | 8/2002 | Bacher |
| 6,443,952 | B1 | 9/2002 | Mulier et al. |
| 6,443,970 | B1 | 9/2002 | Schulze et al. |
| 6,451,018 | B1 | 9/2002 | Lands et al. |
| 6,458,125 | B1 | 10/2002 | Cosmescu |
| 6,458,128 | B1 | 10/2002 | Schulze |
| 6,458,130 | B1 | 10/2002 | Frazier et al. |
| 6,461,352 | B2 | 10/2002 | Morgan et al. |
| 6,461,368 | B2 | 10/2002 | Fogarty et al. |
| 6,464,701 | B1 | 10/2002 | Hooven et al. |
| 6,464,702 | B2 | 10/2002 | Schulze et al. |
| 6,464,704 | B2 | 10/2002 | Schmaltz et al. |
| 6,485,489 | B2 | 11/2002 | Teirstein et al. |
| 6,494,888 | B1 | 12/2002 | Laufer et al. |
| 6,500,176 | B1 | 12/2002 | Truckai et al. |
| 6,503,248 | B1 | 1/2003 | Levine |
| 6,506,189 | B1 | 1/2003 | Rittman, III et al. |
| 6,506,196 | B1 | 1/2003 | Laufer |
| 6,508,815 | B1 | 1/2003 | Strul et al. |
| 6,511,480 | B1 | 1/2003 | Tetzlaff et al. |
| 6,514,215 | B1 | 2/2003 | Ouchi |
| 6,514,251 | B1 | 2/2003 | Ni et al. |
| 6,514,252 | B2 | 2/2003 | Nezhat et al. |
| 6,517,539 | B1 | 2/2003 | Smith et al. |
| 6,527,771 | B1 | 3/2003 | Weadock et al. |
| 6,533,784 | B2 | 3/2003 | Truckai et al. |
| 6,544,264 | B2 | 4/2003 | Levine et al. |
| 6,545,239 | B2 | 4/2003 | Spedale et al. |
| 6,558,385 | B1 | 5/2003 | McClurken et al. |
| 6,562,037 | B2 | 5/2003 | Paton et al. |
| 6,569,105 | B1 | 5/2003 | Kortenbach et al. |
| 6,569,162 | B2 | 5/2003 | He |
| 6,582,450 | B2 | 6/2003 | Ouchi |
| 6,585,735 | B1 | 7/2003 | Frazier et al. |
| 6,602,252 | B2 | 8/2003 | Mollenauer |
| 6,605,790 | B2 | 8/2003 | Yoshida |
| 6,616,658 | B2 | 9/2003 | Ineson |
| 6,616,661 | B2 | 9/2003 | Wellman et al. |
| 6,620,161 | B2 | 9/2003 | Schulze et al. |
| 6,620,184 | B2 | 9/2003 | de Laforcade et al. |
| 6,626,901 | B1 | 9/2003 | Treat et al. |
| 6,638,287 | B2 | 10/2003 | Danitz et al. |
| 6,641,595 | B1 | 11/2003 | Moran et al. |
| 6,652,514 | B2 | 11/2003 | Ellman et al. |
| 6,652,521 | B2 | 11/2003 | Schulze |
| 6,656,175 | B2 | 12/2003 | Francischelli et al. |
| 6,656,177 | B2 | 12/2003 | Truckai et al. |
| 6,660,072 | B2 | 12/2003 | Chatterjee |
| 6,663,639 | B1 | 12/2003 | Laufer et al. |
| 6,663,641 | B1 | 12/2003 | Kovac et al. |
| 6,666,854 | B1 | 12/2003 | Lange |
| 6,669,696 | B2 | 12/2003 | Bacher et al. |
| 6,673,092 | B1 | 1/2004 | Bacher |
| 6,676,660 | B2 | 1/2004 | Wampler et al. |
| 6,676,676 | B2 | 1/2004 | Danitz et al. |
| 6,679,882 | B1 | 1/2004 | Komerup |
| 6,682,527 | B2 | 1/2004 | Strul |
| 6,682,528 | B2 | 1/2004 | Frazier et al. |
| 6,685,724 | B1 | 2/2004 | Haluck |
| 6,689,131 | B2 | 2/2004 | McClurken |
| 6,692,445 | B2 | 2/2004 | Roberts et al. |
| 6,693,246 | B1 | 2/2004 | Rudolph et al. |
| 6,695,840 | B2 | 2/2004 | Schulze |
| 6,702,810 | B2 | 3/2004 | McClurken et al. |
| 6,723,092 | B2 | 4/2004 | Brown et al. |
| 6,726,068 | B2 | 4/2004 | Miller |
| 6,726,686 | B2 * | 4/2004 | Buysse ............ A61B 18/1442 606/51 |
| 6,726,694 | B2 | 4/2004 | Blatter et al. |
| 6,733,498 | B2 | 5/2004 | Paton et al. |
| 6,736,813 | B2 | 5/2004 | Yamauchi et al. |
| 6,743,229 | B2 | 6/2004 | Buysse et al. |
| 6,743,230 | B2 | 6/2004 | Lutze et al. |
| 6,743,239 | B1 | 6/2004 | Kuehn et al. |
| 6,743,240 | B2 | 6/2004 | Smith et al. |
| 6,755,843 | B2 | 6/2004 | Chung et al. |
| 6,756,553 | B1 | 6/2004 | Yamaguchi et al. |
| 6,757,977 | B2 | 7/2004 | Dambal et al. |
| D493,888 | S | 8/2004 | Reschke |
| 6,770,072 | B1 | 8/2004 | Truckai et al. |
| 6,773,409 | B2 | 8/2004 | Truckai et al. |
| 6,773,432 | B1 | 8/2004 | Clayman et al. |
| 6,773,434 | B2 | 8/2004 | Ciarrocca |
| 6,773,441 | B1 | 8/2004 | Laufer et al. |
| 6,775,575 | B2 | 8/2004 | Bommannan et al. |
| 6,776,780 | B2 | 8/2004 | Mulier et al. |
| 6,786,905 | B2 | 9/2004 | Swanson et al. |
| 6,790,217 | B2 | 9/2004 | Schulze et al. |
| 6,796,981 | B2 | 9/2004 | Wham et al. |
| D496,997 | S | 10/2004 | Dycus et al. |
| 6,800,825 | B1 | 10/2004 | Sasaki et al. |
| 6,802,843 | B2 | 10/2004 | Truckai et al. |
| 6,808,525 | B2 | 10/2004 | Latterell et al. |
| D499,181 | S | 11/2004 | Dycus et al. |
| 6,818,000 | B2 | 11/2004 | Muller et al. |
| 6,821,285 | B2 | 11/2004 | Laufer et al. |
| 6,835,200 | B2 | 12/2004 | Laufer et al. |
| 6,857,357 | B2 | 2/2005 | Fujii |
| 6,860,880 | B2 | 3/2005 | Treat et al. |
| 6,887,240 | B1 | 5/2005 | Lands et al. |
| 6,889,116 | B2 | 5/2005 | Jinno |
| 6,914,201 | B2 | 7/2005 | Van Vooren et al. |
| 6,926,716 | B2 | 8/2005 | Baker et al. |
| 6,929,644 | B2 | 8/2005 | Truckai et al. |
| 6,932,810 | B2 | 8/2005 | Ryan |
| 6,932,816 | B2 | 8/2005 | Phan |
| 6,934,134 | B2 | 8/2005 | Mori et al. |
| 6,936,061 | B2 | 8/2005 | Sasaki |
| D509,297 | S | 9/2005 | Wells |
| 6,942,662 | B2 | 9/2005 | Goble et al. |
| 6,943,311 | B2 | 9/2005 | Miyako |
| 6,953,430 | B2 | 10/2005 | Kidooka |
| 6,953,461 | B2 | 10/2005 | McClurken et al. |
| 6,958,070 | B2 | 10/2005 | Witt et al. |

(56) References Cited

U.S. PATENT DOCUMENTS

| | | |
|---|---|---|
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,011,657 B2 | 3/2006 | Truckai et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,112,199 B2 | 9/2006 | Cosmescu |
| D531,311 S | 10/2006 | Guerra et al. |
| 7,115,123 B2 | 10/2006 | Knowlton et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,020 B2 | 11/2006 | Lawes et al. |
| D533,942 S | 12/2006 | Kerr et al. |
| 7,145,757 B2 | 12/2006 | Shea et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |
| 7,160,298 B2 | 1/2007 | Lawes et al. |
| 7,160,299 B2 | 1/2007 | Baily |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,195,631 B2 | 3/2007 | Dumbauld |
| D541,418 S | 4/2007 | Schechter et al. |
| 7,207,990 B2 | 4/2007 | Lands et al. |
| D541,938 S | 5/2007 | Kerr et al. |
| 7,223,264 B2 | 5/2007 | Daniel et al. |
| 7,223,265 B2 | 5/2007 | Keppel |
| 7,232,440 B2 | 6/2007 | Dumbauld et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,248,944 B2 | 7/2007 | Green |
| 7,252,667 B2 | 8/2007 | Moses et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| D567,943 S | 4/2008 | Moses et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,336 B2 | 7/2008 | Orszulak et al. |
| D575,395 S | 8/2008 | Hushka |
| D575,401 S | 8/2008 | Hixson et al. |
| 7,435,249 B2 | 10/2008 | Buysse et al. |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,510,556 B2 | 3/2009 | Nguyen et al. |
| 7,513,898 B2 | 4/2009 | Johnson et al. |
| 7,536,749 B2 * | 5/2009 | Lu .................. G06F 1/1616 16/330 |
| 7,540,872 B2 | 6/2009 | Schechter et al. |
| 7,549,995 B2 | 6/2009 | Schultz |
| 7,553,312 B2 | 6/2009 | Tetzlaff et al. |
| 8,333,765 B2 | 12/2012 | Johnson et al. |
| 2002/0013583 A1 | 1/2002 | Camran et al. |
| 2002/0049442 A1 | 4/2002 | Roberts et al. |
| 2002/0099372 A1 | 7/2002 | Schulze et al. |
| 2002/0107517 A1 | 8/2002 | Witt et al. |
| 2002/0111624 A1 | 8/2002 | Witt et al. |
| 2002/0188294 A1 | 12/2002 | Couture et al. |
| 2003/0014052 A1 | 1/2003 | Buysse et al. |
| 2003/0014053 A1 | 1/2003 | Nguyen et al. |
| 2003/0018331 A1 | 1/2003 | Dycus et al. |
| 2003/0018332 A1 | 1/2003 | Schmaltz et al. |
| 2003/0032956 A1 | 2/2003 | Lands et al. |
| 2003/0069570 A1 | 4/2003 | Witzel et al. |
| 2003/0069571 A1 | 4/2003 | Treat et al. |
| 2003/0078577 A1 | 4/2003 | Truckai et al. |
| 2003/0078578 A1 | 4/2003 | Truckai et al. |
| 2003/0109875 A1 | 6/2003 | Tetzlaff et al. |
| 2003/0114851 A1 | 6/2003 | Truckai et al. |
| 2003/0139741 A1 | 7/2003 | Goble et al. |
| 2003/0139742 A1 | 7/2003 | Wampler et al. |
| 2003/0158548 A1 | 8/2003 | Phan et al. |
| 2003/0158549 A1 | 8/2003 | Swanson |
| 2003/0171747 A1 | 9/2003 | Kanehira et al. |
| 2003/0181910 A1 | 9/2003 | Dycus et al. |
| 2003/0199869 A1 | 10/2003 | Johnson et al. |
| 2003/0216732 A1 | 11/2003 | Truckai et al. |
| 2003/0220637 A1 | 11/2003 | Truckai et al. |
| 2003/0229344 A1 | 12/2003 | Dycus et al. |
| 2003/0236325 A1 | 12/2003 | Bonora |
| 2003/0236518 A1 | 12/2003 | Marchitto et al. |
| 2004/0030330 A1 | 2/2004 | Brassell et al. |
| 2004/0030332 A1 | 2/2004 | Knowlton et al. |
| 2004/0049185 A1 | 3/2004 | Latterell et al. |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |

(56) References Cited

U.S. PATENT DOCUMENTS

| | | |
|---|---|---|
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0193153 A1 | 9/2004 | Sartor et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter et al. |
| 2005/0004564 A1 | 1/2005 | Wham et al. |
| 2005/0004568 A1 | 1/2005 | Lawes et al. |
| 2005/0004569 A1 | 1/2005 | Witt et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113828 A1 | 5/2005 | Shields et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0264931 A1 | 11/2006 | Chapman et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015567 A1 | 1/2008 | Kimura |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0112206 A1 | 4/2009 | Dumbauld et al. |
| 2009/0131934 A1 | 5/2009 | Odom et al. |
| 2009/0149853 A1 | 6/2009 | Shields et al. |
| 2009/0149854 A1 | 6/2009 | Cunningham et al. |
| 2009/0171350 A1 | 7/2009 | Dycus et al. |
| 2009/0171353 A1 | 7/2009 | Johnson et al. |
| 2009/0182327 A1 | 7/2009 | Unger |
| 2009/0187188 A1 | 7/2009 | Guerra et al. |

(56) References Cited

U.S. PATENT DOCUMENTS

| | | | |
|---|---|---|---|
| 2010/0000049 A1* | 1/2010 | Lin | G06F 1/1616 16/340 |
| 2011/0071523 A1 | 3/2011 | Dickhans | |
| 2012/0029554 A1* | 2/2012 | Kreidler | A61B 17/2812 606/205 |

FOREIGN PATENT DOCUMENTS

| | | |
|---|---|---|
| DE | 02514501 A1 | 10/1976 |
| DE | 2627679 A1 | 1/1977 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19828976 A1 | 2/2000 |
| DE | 20001204 U1 | 3/2000 |
| DE | 19738457 B4 | 1/2009 |
| EP | 0467501 A1 | 1/1992 |
| EP | 0541930 A1 | 5/1993 |
| EP | 0572131 A1 | 12/1993 |
| EP | 0584787 A1 | 3/1994 |
| EP | 0589555 A1 | 3/1994 |
| EP | 0589453 A3 | 4/1994 |
| EP | 0624348 A3 | 6/1995 |
| EP | 0364216 B1 | 1/1996 |
| EP | 0518230 B1 | 5/1996 |
| EP | 0517243 B1 | 9/1997 |
| EP | 0878169 A1 | 11/1998 |
| EP | 0623316 B1 | 3/1999 |
| EP | 0650701 B1 | 3/1999 |
| EP | 0923907 A1 | 6/1999 |
| EP | 0986990 A1 | 3/2000 |
| EP | 1034747 A1 | 9/2000 |
| EP | 1034748 | 9/2000 |
| EP | 0694290 B1 | 11/2000 |
| EP | 1050278 | 11/2000 |
| EP | 1053719 | 11/2000 |
| EP | 1053720 | 11/2000 |
| EP | 1055399 | 11/2000 |
| EP | 1055400 | 11/2000 |
| EP | 1080694 | 3/2001 |
| EP | 1082944 | 3/2001 |
| EP | 1177771 | 2/2002 |
| EP | 1159926 A3 | 3/2003 |
| EP | 0717966 B1 | 4/2003 |
| EP | 1301135 | 4/2003 |
| EP | 0887046 B1 | 7/2003 |
| EP | 1330991 A1 | 7/2003 |
| EP | 1486177 | 6/2004 |
| EP | 1472984 | 11/2004 |
| EP | 0754437 B2 | 12/2004 |
| EP | 1025807 B1 | 12/2004 |
| EP | 0774232 B1 | 1/2005 |
| EP | 0853922 B1 | 2/2005 |
| EP | 1527747 | 5/2005 |
| EP | 1530952 | 5/2005 |
| EP | 1532932 A1 | 5/2005 |
| EP | 1535581 | 6/2005 |
| EP | 1609430 A1 | 12/2005 |
| EP | 1034746 B1 | 3/2006 |
| EP | 1632192 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 0875209 B1 | 5/2006 |
| EP | 1707143 A1 | 10/2006 |
| EP | 1769765 A1 | 4/2007 |
| EP | 1769766 | 4/2007 |
| EP | 1929970 | 6/2008 |
| EP | 1683496 | 12/2008 |
| EP | 2591744 A1 | 5/2013 |
| GB | 221341 A | 9/1924 |
| GB | 221443 A | 9/1924 |
| GB | 623316 | 5/1949 |
| GB | 1490585 | 11/1977 |
| GB | 2213416 A | 8/1989 |
| GB | 2214430 A | 9/1989 |
| JP | 61-501068 | 9/1984 |
| JP | 6-502328 | 3/1992 |
| JP | 5-5106 | 1/1993 |
| JP | 05-40112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 09010223 | 1/1997 |
| JP | 11244298 A | 9/1999 |
| JP | 2000252831 A | 9/2000 |
| JP | 2000289472 A | 10/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001128990 A | 5/2001 |
| SU | 401367 A1 | 10/1973 |
| WO | 89/00757 | 1/1989 |
| WO | 92/04873 | 4/1992 |
| WO | 92/06642 | 4/1992 |
| WO | 93/21845 | 11/1993 |
| WO | 94/08524 | 4/1994 |
| WO | 94/20025 | 9/1994 |
| WO | 95/02369 | 1/1995 |
| WO | 95/07662 | 3/1995 |
| WO | 95/15124 | 6/1995 |
| WO | 96/5776 | 2/1996 |
| WO | 96-22056 A1 | 7/1996 |
| WO | 96/13218 | 9/1996 |
| WO | 97/00646 | 1/1997 |
| WO | 97/00647 | 1/1997 |
| WO | 97/10764 | 3/1997 |
| WO | 97/24073 | 7/1997 |
| WO | 97/24993 | 7/1997 |
| WO | 98/27880 | 7/1998 |
| WO | 99/03407 | 1/1999 |
| WO | 99/03408 | 1/1999 |
| WO | 99/03409 | 1/1999 |
| WO | 99/12488 | 3/1999 |
| WO | 96-23933 A2 | 5/1999 |
| WO | 99/40857 | 8/1999 |
| WO | 99/40861 | 8/1999 |
| WO | 99/51158 | 10/1999 |
| WO | 99/66850 | 12/1999 |
| WO | 00/24330 | 5/2000 |
| WO | 00/24331 | 5/2000 |
| WO | 0036986 A1 | 6/2000 |
| WO | 00/41638 | 7/2000 |
| WO | 00/47124 | 8/2000 |
| WO | 00/53112 | 9/2000 |
| WO | 01/17448 | 3/2001 |
| WO | 0154604 A1 | 8/2001 |
| WO | 0166026 A2 | 9/2001 |
| WO | 02/07627 | 1/2002 |
| WO | 02/067798 | 9/2002 |
| WO | 02/080783 | 10/2002 |
| WO | 02/080784 | 10/2002 |
| WO | 02/080785 | 10/2002 |
| WO | 02/080786 | 10/2002 |
| WO | 02/080793 | 10/2002 |
| WO | 02/080794 | 10/2002 |
| WO | 02/080795 | 10/2002 |
| WO | 02/080797 | 10/2002 |
| WO | 02/080798 | 10/2002 |
| WO | 02/080799 | 10/2002 |
| WO | 02/081170 | 10/2002 |
| WO | 02080796 A1 | 10/2002 |
| WO | 02098313 A1 | 12/2002 |
| WO | 03/061500 | 7/2003 |

(56) References Cited

FOREIGN PATENT DOCUMENTS

| WO | 03/101311 | 12/2003 |
|---|---|---|
| WO | 03/090630 A3 | 4/2004 |
| WO | 2004/032776 A1 | 4/2004 |
| WO | 2004/032777 A1 | 4/2004 |
| WO | 2004/052221 A1 | 6/2004 |
| WO | 04/073490 A2 | 9/2004 |
| WO | 2004/073488 A2 | 9/2004 |
| WO | 2004/073753 A2 | 9/2004 |
| WO | 2004/082495 A1 | 9/2004 |
| WO | 2004/098383 A2 | 11/2004 |
| WO | 04/103156 | 12/2004 |
| WO | 2005/004734 A1 | 1/2005 |
| WO | 2005/004735 A1 | 1/2005 |
| WO | 2005/110264 A2 | 11/2005 |
| WO | 2008/045348 A2 | 4/2008 |
| WO | 2008/045350 A2 | 4/2008 |
| WO | 2013009756 A2 | 1/2013 |

OTHER PUBLICATIONS

Bergdahl et al., Studies on Coagulation and the Development of an Automatic Computerized Bipolar Coagulator, J. Neurosurg. vol. 75, Jul. 1991 pp. 148-151.

US 6,090,109, Jul. 2000, Lands et al. (withdrawn).

US 6,663,629, Dec. 2003, Buysse et al. (withdrawn).

Kennedy et al. "High-burst-strength, feedback-controlled bipolar vessel sealing" Surgical Endoscopy (1998) 12:376-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectormy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrothermal Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics FIGO World Congress 2000, Washington, D.C.

Levy et al. "Use of a New Energy-based Vessel Ligation Device During Vaginal Hysterectomy" Int'l Federation of Gynecology and Obstetrics (FIGO) World Congress.

Crawford et al. "Use of the LigaSure Vessel Sealing System in Urologic Cancer Surger" Grand Rounds in Urology 1999 vol. 1 Issue 4 pp. 10-17.

Rothenberg et al. "Use of the LigaSure Vessel Sealing System in Minimally Invasive Surgery in Children" Int'l Pediatric Endosurgery Group (IPEG) 2000.

Palazzo et al. "Randomized clinical trial of Ligasure versus open haemorrhoidectomy" British Journal of Surgery 2002, 39, 154-157.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte,NC.

"Reducing Needlestick Injuries in the Operating Room" Sales/Product Literature.

Chung et al., "Clinical Experience of Sutureless Closed Hemorrhoidectomy with LigaSure" Diseases of the Colon & Rectum vol. 46, No. Jan. 1, 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature.

Michael Choti, "Abdominoperineal Resection with the LigaSure Vessel Sealing System and LigaSure Atlas 20 cm Open Instrument" Innovations That Work, Jun. 2003.

Muller et al., "Extended Left Hemicolectomy Using the LigaSure Vessel Sealing System" Innovations That Work, Sep. 1999.

Herman et al., "Laparoscopic Intestinal Resection With the LigaSure Vessel Sealing System: A Case Report" Innovations That Work, Feb. 2002.

Carus et al., "Initial Experience With the LigaSure Vessel Sealing System in Abdominal Surgery" Innovations That Work, Jun. 2002.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al. "Vessel Sealing for Hemostasis During Gynecologic Surgery" Sales Product Literature.

Sengupta et al., "Use of a Computer-Controlled Bipolar Diathermy System in Radical Prostatectomies and Other Open Urological Surgery" ANZ Journal of Surgery (2001) 71.9 pp. 538-540.

Olsson et al. "Radical Cystectomy in Females" Current Surgical Techniques in Urology, vol. 14, Issue 3.

E. David Crawford "Use of a Novel Vessel Sealing Technology in Management of the Dorsal Veinous Complex" Sales Product Literature.

Jarrett et al., "Use of the LigaSure Vessel Sealing System for Peri-Hilar Vessels in Laparoscopic Nephrectomy" Sales Product Literature.

E. David Crawford "Evaluation of a New Vessel Sealing Device in Urologic Cancer Surgery" Sales Product Literature.

Dulemba et al., "Use of a Bipolar Electrothermal Vessel Sealer in Laparoscopically Assisted Vaginal Hysterectomy" Sales Product Literature.

Johnson et al., "Evaluation of a Bipolar electrothermal Vessel Sealing Device in Hemorrhoidectomy" Sales Product Literature.

"Innovations in Electrosurgery" Sales/Product Literature: Dec. 31, 2000.

LigaSure Vessel Sealing System, the Seal of Confidence in General, Gynecologic, Urologic, and Laparaoscopic Surgery Sales/Product Literature: Jan. 2004.

Craig Johnson. "Use of the LigaSure Vessel Sealing System in Bloodless Hemorrhoidectomy" That Work, Mar. 2000.

Joseph Ortenberg "LigaSure System Used in Laparoscopic 1st and 2nd Stage Orchiopexy" Innovations That Work, Nov. 2002.

Koyle et al., "Laparoscopic Palomo Varicocele Ligation in Children and Adolescents" Pediatric Endosurgery & Innovative Techniques, vol. 6, No. 1, 2002.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Crouch et al. "A Velocity-Dependent Model for Needle Insertion in Soft Tissue" MICCAI 2005; LNCS 3750 pp. 624-632 Dated: 2005.

The International Search Report and Written Opinion dated Apr. 30, 2014 issued in corresponding PCT Appln. No. PCT/CN2013/080948.

* cited by examiner

SURGICAL FORCEPS

CROSS REFERENCE TO RELATED APPLICATION

The present application is a U.S. National Stage Application under 35 U.S.C. § 371(a) of PCT/CN2013/080948 filed Aug. 7, 2013, the entire contents of which are incorporated by reference herein.

BACKGROUND

Technical Field

The present disclosure relates to a surgical devices and, more particularly, to surgical forceps for grasping, treating, and/or cutting tissue.

Background of Related Art

A forceps is a plier-like instrument which relies on mechanical action between its jaws to grasp, clamp, and constrict tissue. Electrosurgical forceps utilize both mechanical clamping action and electrical energy to affect hemostasis by heating tissue to coagulate and/or cauterize tissue. Certain surgical procedures require more than simply cauterizing tissue and rely on the unique combination of clamping pressure, precise electrosurgical energy control, and gap distance (i.e., distance between opposing jaw members when closed about tissue) to "seal" tissue. Typically, once tissue is sealed, the surgeon has to accurately sever the tissue along the newly formed tissue seal. Accordingly, many tissue-sealing instruments have been designed which incorporate a knife or blade member which effectively severs the tissue after forming a tissue seal. Alternatively or additionally, energy-based tissue division may be effected.

SUMMARY

As used herein, the term "distal" refers to the portion that is being described which is further from a user, while the term "proximal" refers to the portion that is being described which is closer to a user. Further, to the extent consistent, any of the aspects described herein may be used in conjunction with any or all of the other aspects described herein.

In accordance with aspects of the present disclosure, an end effector assembly for a surgical device is provided. The end effector assembly includes first and second jaw members pivotable relative to one another between a spaced-apart position and an approximated position for grasping tissue therebetween. The first and second jaw members include first and second proximal flanges, respectively. A pivot pin couples the proximal flanges of the jaw members to one another to permit pivoting of the jaw members between the spaced-apart and approximated positions. The pivot pin includes a body and a head. The body is coupled to the first proximal flange, while the head defines a first ramped surface configured to slidably contact a second ramped surface of the second proximal flange. In the spaced-apart position of the jaw members, the first and second ramped surfaces are oppositely disposed such that a maximum clearance is defined between the first and second proximal flanges. In the approximated position of the jaw members, the first and second ramped surfaces are similarly disposed such that a minimum clearance is defined between the first and second proximal flanges.

In aspects, the first ramped surface includes first and second ramped segments interconnected by first and second steps, and the second ramped surface includes third and fourth ramped segments interconnected by third and fourth steps. In such aspects, in the spaced-apart position of the jaw members, the first and third ramped segments are disposed adjacent one another, the second and fourth ramped surfaces are disposed adjacent one another, the first and third steps are disposed adjacent one another, and the second and fourth steps are disposed adjacent one another. On the other hand, in the approximated position of the jaw members, the first and fourth ramped segments are disposed adjacent one another, the second and third ramped surfaces are disposed adjacent one another, the first and fourth steps are disposed adjacent one another, and the second and third steps are disposed adjacent one another.

In aspects, the first and second ramped surfaces are radially sloped in similar directions.

In aspects, a portion of the body of the pivot pin is fixedly engaged within an aperture defined through the first proximal flange, e.g., via laser welding.

In aspects, each jaw member further includes a distal jaw portion defining a tissue-contacting surface. The tissue-contacting surfaces are configured to grasp tissue therebetween upon movement of the jaw members to the approximated position.

In aspects, one or both of the jaw members is adapted to connect to a source of energy for conducting energy between the tissue-contacting surfaces and through tissue grasped therebetween to treat tissue.

In aspects, when the maximum clearance is defined between the proximal flanges, some degree of lateral movement and tilting of the jaw members relative to one another is permitted. On the other hand, when the minimum clearance is defined between the proximal flanges, the jaw members are maintained in alignment with one another.

Another end effector assembly for a surgical device provided in accordance with aspects of the present disclosure includes a first jaw member, a second jaw member, and a pivot pin. The first jaw member includes a first proximal flange portion and a first distal jaw portion. The first proximal flange portion defines a first aperture extending therethrough. The second jaw member includes a second proximal flange portion and a second distal jaw portion. The second proximal flange portion defines a second aperture and has a shoulder disposed about the second aperture. The shoulder defines a first ramped surface. The pivot pin includes a body and a head. The body extends through the second aperture and is engaged within the first aperture. The head defines a second ramped surface slidably contacting the first ramped surface of the shoulder. The second proximal flange is retained about the body of the pivot pin between the first proximal flange and the head, and is pivotable about the body of the pivot pin and relative to the first proximal flange for moving the jaw members between a spaced-apart position and an approximated position. The first and second ramped surfaces are configured such that, in the spaced-apart position of the jaw members, a maximum clearance is defined between the first and second proximal flanges, and such that, in the approximated position of the jaw members, a minimum clearance is defined between the first and second proximal flanges.

In aspects, in the spaced-apart position of the jaw members, the first and second ramped surfaces are oppositely disposed to define the maximum clearance. In aspects, in the approximated position of the jaw members, the first and second ramped surfaces are similarly disposed to define the minimum clearance.

In aspects, when the maximum clearance is defined between the proximal flanges, at least some degree of lateral movement and tilting of the jaw members relative to one another is permitted. In aspects, when the minimum clearance is defined between the proximal flanges, the jaw members are maintained in alignment with one another.

In aspects, the first ramped surface includes first and second ramped segments interconnected by first and second steps, and the second ramped surface includes third and fourth ramped segments interconnected by third and fourth steps. In such aspects, in the spaced-apart position of the jaw members, the first and third ramped segments are disposed adjacent one another, the second and fourth ramped surfaces are disposed adjacent one another, the first and third steps are disposed adjacent one another, and the second and fourth steps are disposed adjacent one another. On the other hand, in the approximated position of the jaw members, the first and fourth ramped segments are disposed adjacent one another, the second and third ramped surfaces are disposed adjacent one another, the first and fourth steps are disposed adjacent one another, and the second and third steps are disposed adjacent one another.

In aspects, the first and second ramped surfaces are radially sloped in similar directions.

In aspects, the body of the pivot pin is laser welded within the aperture of the first proximal flange.

In aspects, each of the distal jaw portions defines a tissue-contacting surface. In such aspects, one or both of the tissue-contacting surfaces is adapted to connect to a source of energy for conducting energy between the tissue-contacting surfaces and through tissue to treat tissue.

BRIEF DESCRIPTION OF THE DRAWINGS

Various aspects and features of the present disclosure are described herein with reference to the drawings wherein.

DETAILED DESCRIPTION

Figure 1:
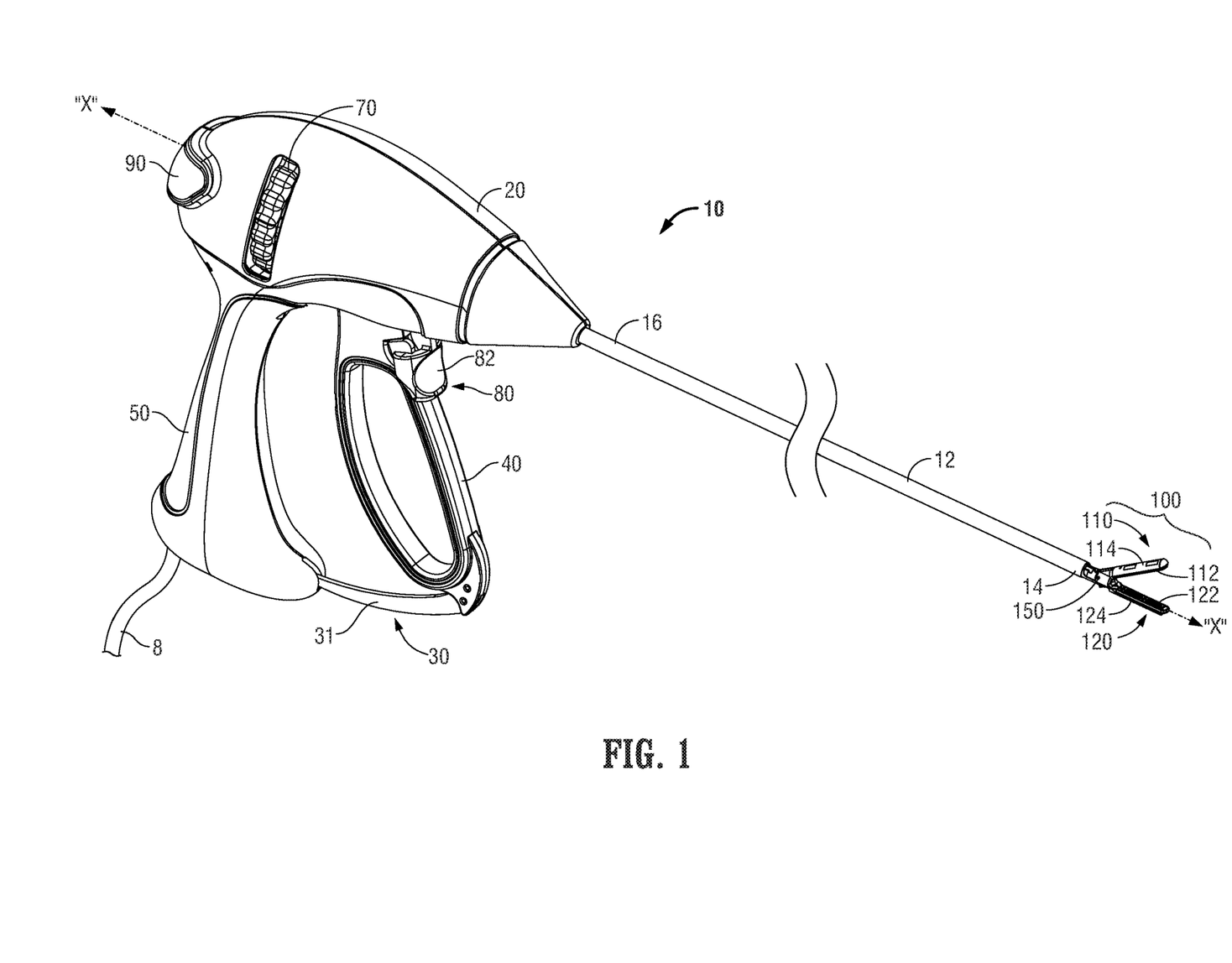
FIG. 1 is a front, side, perspective view of an endoscopic surgical forceps configured for use in accordance with the present disclosure.
Figures 2A, 2B:
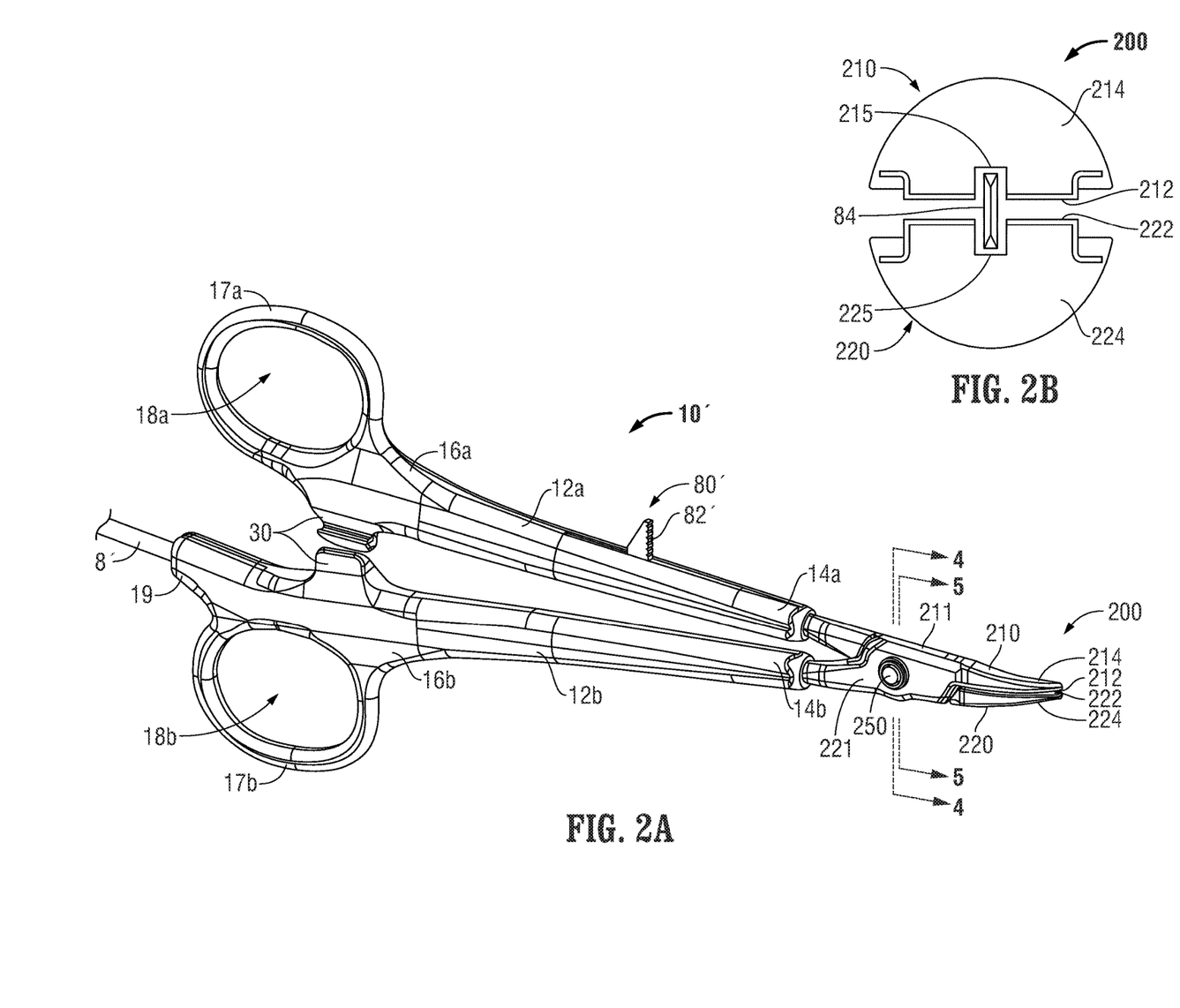
FIG. 2A is a front, side, perspective view of an open surgical forceps configured for use in accordance with the present disclosure.
FIG. 2B is a transverse, cross-sectional view of the end effector assembly of the forceps of FIG. 2A.
Figures 3A, 3B:
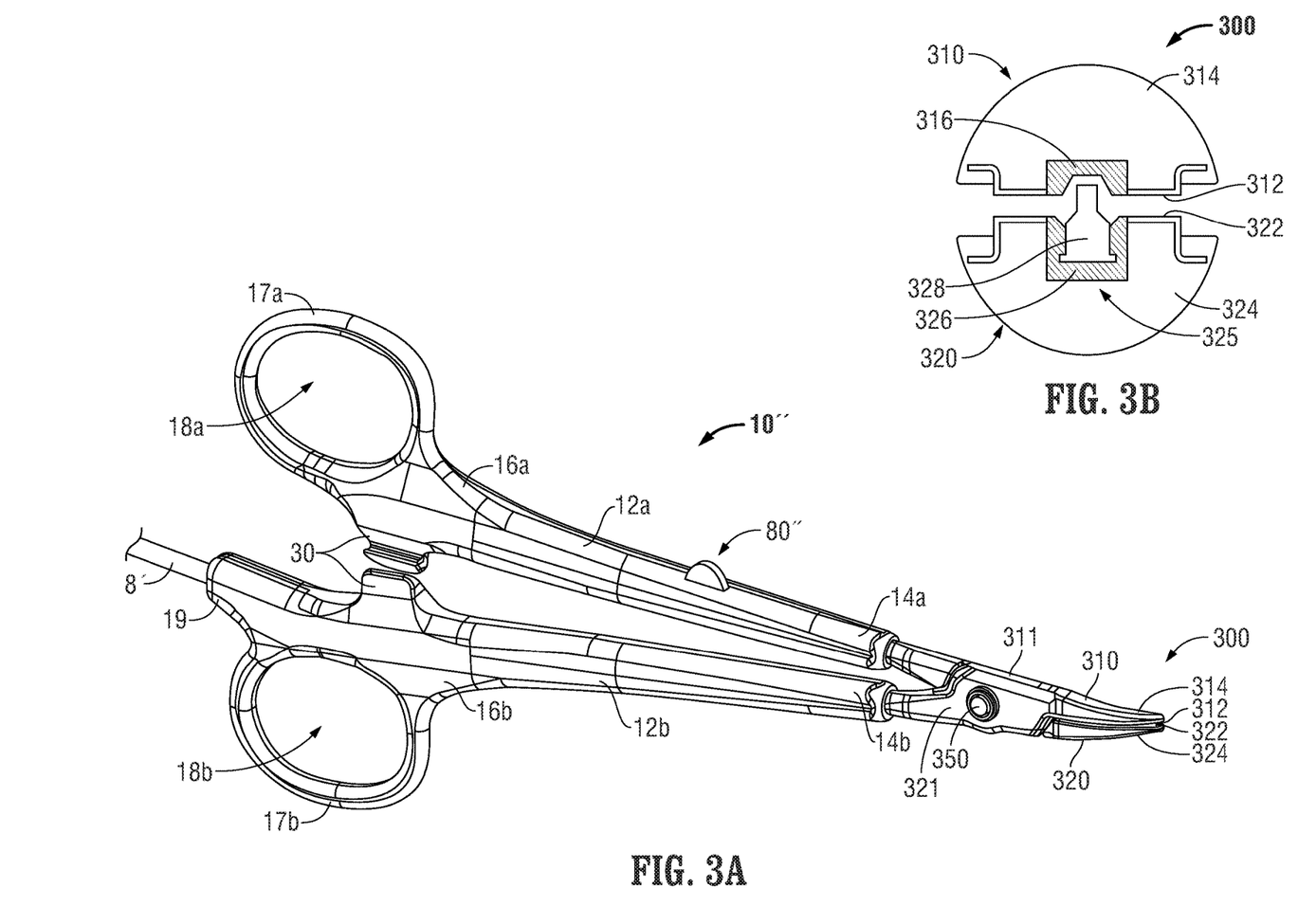
FIG. 3A is a front, side, perspective view of another open surgical forceps configured for use in accordance with the present disclosure.
FIG. 3B is a transverse, cross-sectional view of the end effector assembly of the forceps of FIG. 3A.
Figure 4:
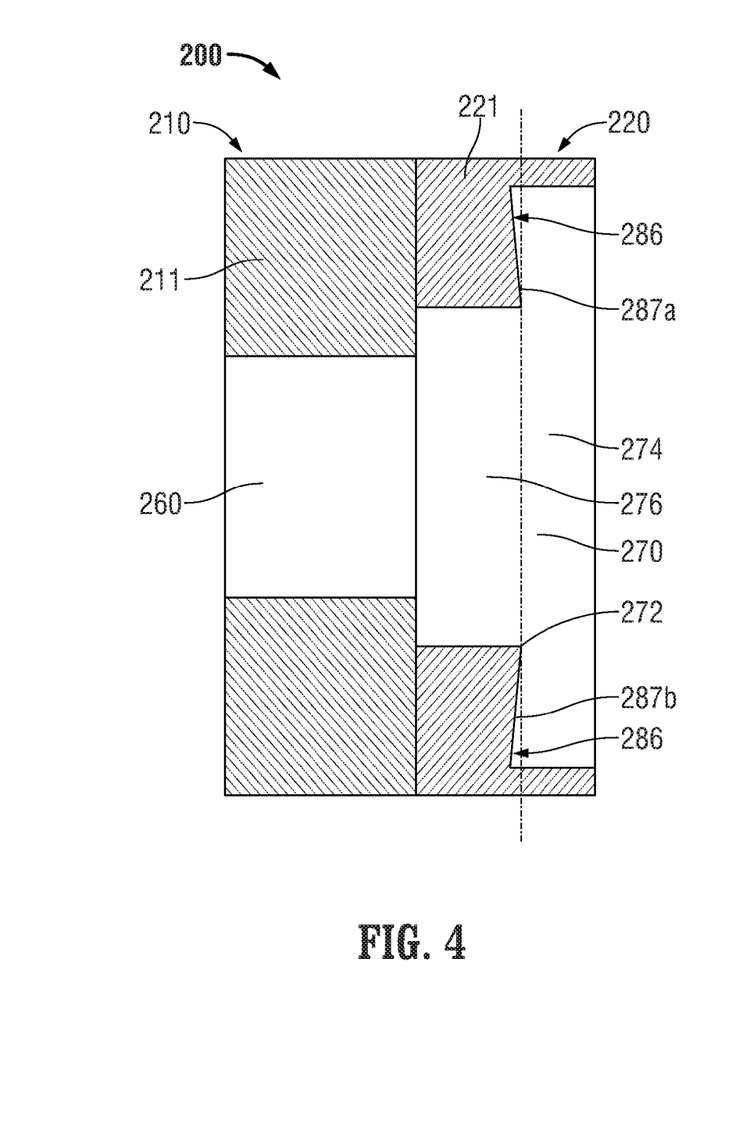
FIG. 4 is a cross-sectional view taken along line 4-4 of FIG. 2A.
Figure 5:
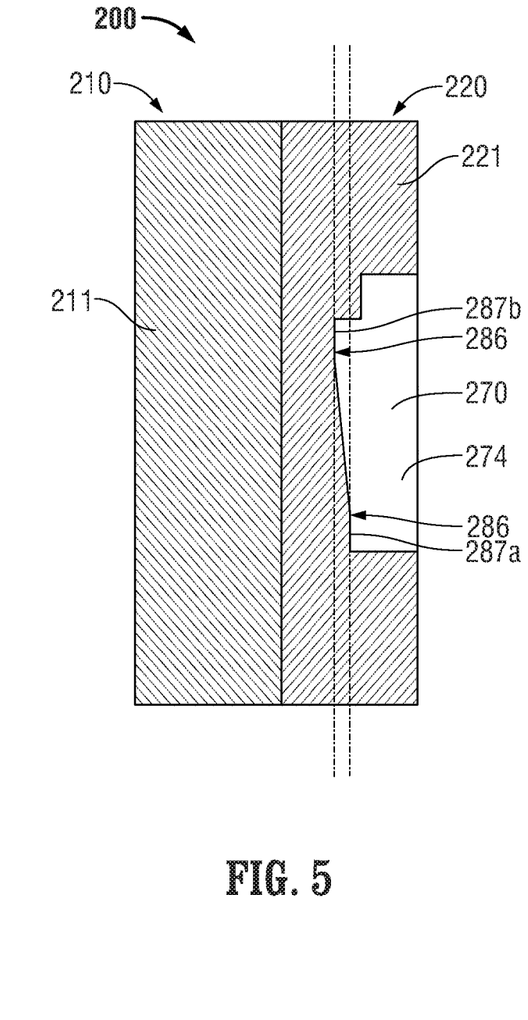
FIG. 5 is a cross-sectional view taken alone line 5-5 of FIG. 2A.

Referring now to FIGS. 1, 2A-2B, and 3A-3B, FIG. 1 depicts an endoscopic surgical forceps 10 configured for use in connection with endoscopic surgical procedures, FIGS. 2A-2B depict a open surgical forceps 10' configured for use in connection with traditional open surgical procedures and FIGS. 3A-3B depict another open surgical forceps 10" configured for use in connection with traditional open surgical procedures. For the purposes herein, either an endoscopic device, e.g., forceps 10, an open device, e.g., forceps 10' or forceps 10", or any other suitable surgical device may be utilized in accordance with the present disclosure. Obviously, different electrical and mechanical connections and considerations apply to each particular type of device, however, the aspects and features of the present disclosure remain generally consistent regardless of the particular device used.

Turning now to FIG. 1, an endoscopic forceps 10 is provided defining a longitudinal axis "X-X" and including a housing 20, a handle assembly 30, a rotating assembly 70, a trigger assembly 80, and an end effector assembly 100. Forceps 10 further includes a shaft 12 having a distal end 14 configured to mechanically engage end effector assembly 100 and a proximal end 16 that mechanically engages housing 20. Forceps 10 also includes cable 8 that connects forceps 10 to an energy source (not shown), e.g., a generator or other suitable power source, although forceps 10 may alternatively be configured as a battery-powered device. Cable 8 includes a wire (or wires) (not shown) extending therethrough that has sufficient length to extend through shaft 12 in order to provide energy to at least one of tissue-contacting surfaces 112, 122 of jaw members 110, 120, respectively. An activation switch 90 is provided on housing 20 for selectively supplying energy to jaw members 110, 120. Rotating assembly 70 is rotatable in either direction about a longitudinal axis "X-X" to rotate end effector assembly 100 about longitudinal axis "X-X." Housing 20 houses the internal working components of forceps 10.

Handle assembly 30 includes a fixed handle 50 and a movable handle 40. Fixed handle 50 is integrally associated with housing 20 and handle 40 is movable relative to fixed handle 50. Movable handle 40 of handle assembly 30 is ultimately connected to a drive assembly (not shown) that, together, mechanically cooperate to impart movement of jaw members 110 and 120 between a spaced-apart position and an approximated position to grasp tissue between jaw members 110, 120. As shown in FIG. 1, movable handle 40 is initially spaced-apart from fixed handle 50 and, correspondingly, jaw members 110, 120 are in the spaced-apart position. Movable handle 40 is depressible from this initial position to a depressed position corresponding to an approximated position of jaw members 110, 120. A ratchet assembly 31 may also be included for selectively locking jaw members 110, 120 relative to one another in one or more approximated positions.

In some embodiments, a knife assembly (not shown) is provided. Trigger 82 of trigger assembly 80 is operably coupled to the knife assembly (not shown) for selectively translating a knife blade (not shown) through a knife channel (not shown) defined within one or both of jaw members 110, 120 to cut tissue grasped between jaw members 110, 120. The knife blade (not shown) may be configured for mechanical cutting, or may be energizable, e.g., via electrical coupling to the source of energy (not shown) via the one or more wires (not shown) of cable 8, for dynamically electromechanically cutting tissue. Alternatively, end effector assembly 100 may include an electrical cutting assembly configured for statically electrically cutting tissue, similarly as will be described below with respect to end effector assembly 300 of forceps 10" (see FIGS. 3A-3B).

With continued reference to FIG. 1, each of jaw members 110, 120 of end effector assembly 100 includes an outer insulative jaw housing 114, 124 and an electrically-conductive tissue-contacting surface 112, 122, respectively. As mentioned above, tissue-contacting surfaces 112, 122 are electrically coupled to activation switch 90 (FIG. 1) and the source of energy (not shown) such that energy may be selectively supplied to tissue-contacting surface 112 and/or tissue-contacting surface 122 and conducted therebetween and through tissue grasped between jaw members 110, 120 to treat, e.g., seal, tissue. End effector assembly 100 is designed as a unilateral assembly, i.e., where jaw member 120 is fixed relative to shaft 12 and jaw member 110 is movable about pivot 150 relative to shaft 12 and fixed jaw member 120. However, end effector assembly 100 may alternatively be configured as a bilateral assembly, i.e., where both jaw member 110 and jaw member 120 are movable about pivot 150 relative to one another and to shaft 12.

Referring now to FIGS. 2A-2B, an open forceps 10' is shown including two elongated shafts 12a, 12b, each having a proximal end 16a, 16b and a distal end 14a, 14b, respectively. An effector assembly 200, similar to end effector assembly 100 (FIG. 1), is attached to distal ends 14a, 14b of shafts 12a, 12b, respectively. More specifically, end effector assembly 200 includes a pair of opposing jaw members 210 and 220 disposed at distal ends 14b, 14a of shafts 12b, 12a, respectively. Jaw members 210, 220 are pivotably connected about a pivot 250.

Each shaft 12a, 12b of forceps 10' includes a handle 17a, 17b disposed at the proximal end 16a, 16b thereof. Each handle 17a, 17b defines a finger hole 18a, 18b therethrough for receiving a finger of the surgeon. As can be appreciated, finger holes 18a, 18b facilitate movement of shafts 12a, 12b relative to one another that, in turn, pivots jaw members 210 and 220 about pivot 250 from an open position, wherein the jaw members 210 and 220 are disposed in spaced-apart relation relative to one another, to a closed position, wherein the jaw members 210 and 220 cooperate to grasp tissue therebetween. A ratchet assembly 30' may be provided for selectively locking jaw members 210 and 220 relative to one another at various positions during pivoting, e.g., at one or more approximated positions. Ratchet assembly 30' may include graduations or other visual markings that enable the surgeon to easily and quickly ascertain and control the amount of closure force desired between jaw members 210 and 220.

With continued reference to FIGS. 2A-2B, one of the shafts, e.g., shaft 12b, includes a proximal shaft connector 19 which is designed to connect the forceps 10' to a source of energy (not shown), e.g., a generator. Proximal shaft connector 19 secures an electrosurgical cable 8' to forceps 10' such that the user may selectively apply energy to jaw members 210 and 220, as needed. One of the shafts, e.g., shaft 12a, includes a trigger assembly 80' having a trigger 82' for selectively advancing a knife blade 84 (FIG. 2B) between jaw members 210, 220 to mechanically cut tissue grasped therebetween, although knife blade 84 (FIG. 2B) may also be configured to be energizable for electromechanically cutting tissue.

End effector assembly 200 of forceps 10' includes first and second jaw members 210, 220, each of which include a proximal flange 211, 221, an outer insulative jaw housing 214, 224 and an electrically-conductive tissue-contacting surface 212, 222, respectively. Tissue-contacting surfaces 212, 222 are electrically coupled to the source of energy (not shown), e.g., via wires (not shown) extending from cable 8', for selectively conducting energy through tissue grasped therebetween to treat, e.g., seal, tissue. Each jaw member 210, 220 further includes a longitudinal slot 215, 225 extending therethrough that, in the approximated position of jaw members 210, 220, cooperate to form a blade channel to facilitate translation of knife blade 84 between jaw members 210, 220 to cut tissue grasped therebetween.

Turning now to FIGS. 3A-3B, forceps 10" is similar to forceps 10' (FIGS. 2A-2B) except that, rather than providing a trigger assembly 80' for selectively advancing a knife blade 84 (FIG. 2B) between jaw members 210, 220 (see FIGS. 2A-2B), end effector assembly 300 of forceps 10" includes an electrical cutting assembly 325 (FIG. 3B) and an activation switch 80" for electrically cutting tissue grasped between jaw members 310, 320.

End effector assembly 300 of forceps 10" includes first and second jaw members 310, 320 pivotable about a pivot 350 between a spaced-apart position and an approximated position for grasping tissue therebetween. Each jaw member 310, 320 includes a proximal flange 311, 321, an insulative jaw housing 314, 324 and an electrically-conductive tissue-contacting surface 312, 322, respectively. Tissue-contacting surfaces 312, 322 are electrically coupled to the source of energy (not shown), e.g., via wires (not shown) extending from cable 8', for selectively conducting energy through tissue grasped therebetween to treat, e.g., seal, tissue in a first mode of operation. Electrical cutting assembly 325 is disposed within one of the jaw members, e.g., jaw member 320, and includes an insulating member 326 and a cutting electrode 328. Insulating member 326 is interdisposed between cutting electrode 328 and tissue-contacting surface 322 to electrically-insulate cutting electrode 328 and tissue-contacting surface 322 from one another. Cutting electrode 328 is electrically coupled to activation switch 80" and the source of energy (not shown), e.g., via one or more wires (not shown), for selectively supplying energy to cutting electrode 328 for conduction through tissue and to either or both of tissue-contacting surfaces 312, 322 to electrically or electromechanically cut tissue in a second mode of operation. An insulating member 316 disposed within a longitudinal slot extending along tissue-contacting surface 312 of jaw member 310 is provided to oppose cutting electrode 328.

Proper alignment of the jaw members has been found to be an important factor in effectively treating, e.g., sealing, tissue, limiting damage to tissue, and cutting tissue (either mechanically, electrically, or electro-mechanically). With respect to treating, e.g., sealing, tissue, proper lateral alignment between the tissue-contacting surfaces maximizes the sealing width, e.g., the width of the area between the tissue-contacting surfaces, while proper tilt alignment maintains a consistent gap distance between the jaw members across the sealing width, both of which contribute to effective tissue treatment. With respect to limiting damage to tissue, offset due to lateral misalignment of the tissue-contacting surfaces may result in increased thermal spread, while tilting misalignment of the tissue-contacting surfaces may result in non-uniform conduction of energy through tissue and non-uniform heating of tissue. With respect to dynamic (mechanical or electromechanical) cutting of tissue, mis-alignment of the jaw members may result in misalignment of the blade slots, thus inhibiting translation of the knife blade therethrough. With respect to static (electrical or electromechanical) cutting, proper alignment of the jaw members helps maintain sufficient and substantially equal spacing between the cutting electrode and tissue-contacting surface of the opposed jaw member so as to reduce current concentrations and provide a more uniform distribution of current flow.

The various features and aspects of the present disclosure described below with reference to FIGS. 4-7 facilitate proper alignment of the jaw members, thus facilitating effective grasping, treating (e.g., sealing), and cutting (mechanically, electrically, or electromechanically) of tissue. For the purposes of simplicity and consistency, these features and aspects will be described hereinbelow with respect to end effector assembly 200 of forceps 10' (FIGS. 2A-2B), although the present disclosure is equally applicable for use with any other suitable end effector assembly or surgical device.

Figure 6:
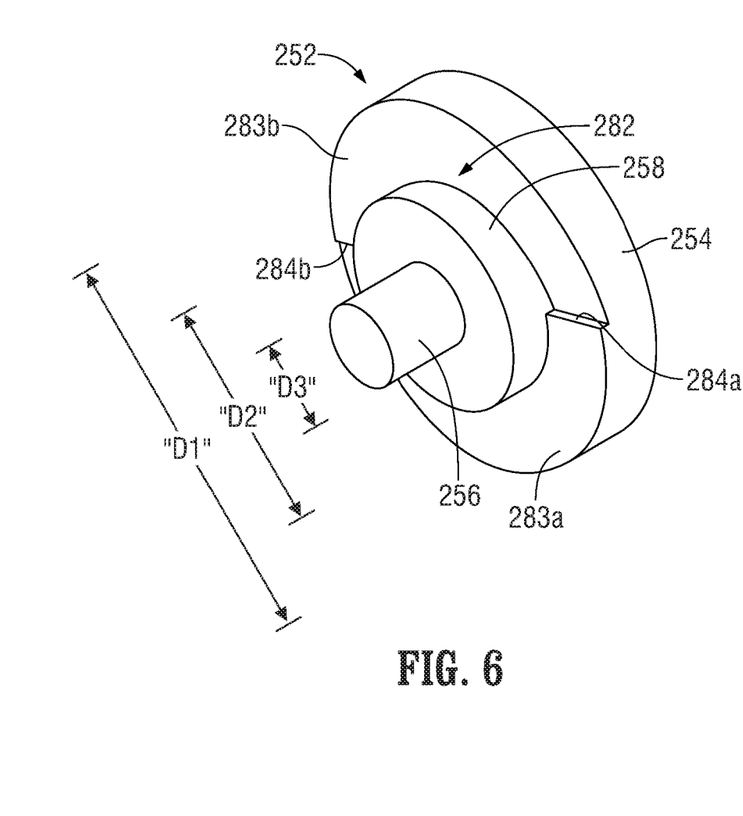
FIG. 6 is a side, perspective view of a pin portion of a pivot for pivotably connecting the jaw members of FIG. 2A.

Turning now to FIGS. 4-7, in conjunction with FIGS. 2A-2B, as mentioned above, jaw members 210, 220 of end effector assembly 200 each include a proximal flange 211, 221, respectively. Proximal flanges 211, 221 are pivotably coupled to one another about pivot 250 to permit movement of jaw members 210, 220 relative to one another between the spaced-apart and approximated positions. With reference to FIG. 6 in particular, pivot 250 includes a pin 252 having a head portion 254 and a body portion that includes a shank portion 256 and a neck portion 258. Neck portion 258 interconnects the head and shank portions 254, 256, respectively, although pin 252 may alternatively include head and shank portions 254, 256 directly connected to one another, e.g., the body portion may only include a shank portion 256 (without neck portion 258). Head portion 254 of pin 252 defines a first diameter "D1," neck portion 258 defines a second diameter "D2" that is smaller than first diameter "D1," and shank portion 256 defines a third diameter "D3" that is smaller than second diameter "D2." Pin 252 may be monolithically formed, or may be manufactured in any other suitable fashion.

Referring again to FIGS. 4-7, in conjunction with FIGS. 2A-2B, pin 252 is configured for insertion through apertures 260, 270, defined transversely through proximal flanges 211, 221 of jaw members 210, 220, respectively, to pivotably couple jaw members 210, 220 to one another. The aperture defined through the proximal flange of one of the jaw members, e.g., aperture 260 of proximal flange 211 of jaw member 210, is configured to receive shank portion 256 of pin 252. As such, aperture 260 defines a diameter that approximates diameter "D3" of shank portion 256 of pin 252. The aperture defined through the proximal flange of the other jaw member, e.g., aperture 270 of proximal flange 221 of jaw member 220, is configured to receive head portion 254 and neck portion 258 of pin 252. More specifically, aperture 270 defines a stepped configuration defining a shoulder 272 that segments aperture 270 into first and second sections 274, 276. First section 274 of aperture 270 is configured to receive head portion 254 of pin 252 and, thus, defines a diameter that approximates diameter "D1" of head portion 254 of pin 252. Second section 276 of aperture 270 is configured to receive neck portion 258 of pin 252 and, thus, defines a diameter that approximates diameter "D2" of neck portion 258 of pin 252.

During assembly of end effector assembly 200, pin 252, lead by shank portion 256, is advanced through aperture 270 of proximal flange 221 of jaw member 220 and into aperture 260 of proximal flange 211 of jaw member 210 until shank portion 256 is disposed within aperture 260. Shank portion 256 is then fixedly secured within aperture 260, e.g., via laser welding or other suitable process, to fix pin 252 relative to jaw member 210, while still permitting jaw member 220 to rotate about pin 252 and relative to jaw member 210. In this configuration, jaw member 220 is retained about pin 252 due to abutment of proximal flange 211 of jaw member 210 and proximal flange 221 of jaw member 220 on one side, and due to the abutment of head portion 254 of pin 252 with shoulder 272 of proximal flange 221 of jaw member 220, on the other side.

Despite the retention of jaw members 210, 220 about pin 252 and relative to one another, lateral movement and/or tilting between jaw members 210, 220 may occur, thus leading to the potential for misalignment between jaw members 210, 220 when approximated about tissue. In fact, at least some clearance is desired between proximal flanges 211, 221 of jaw members 210, 220 so as to permit pivoting of jaw members 210, 220 relative to one another without high force requirements to overcome the frictional forces between proximal flanges 211, 221, respectively. This clearance, however, leads to the potential for lateral movement and/or tilting between the jaw members 210, 220. Thus, a trade-off has typically existed between minimizing clearance (which provides for more accurate jaw alignment) and minimizing the required forces (which allows the jaw members to be more easily pivoted between the spaced-apart and approximated positions). Pivot 250 and jaw member 210, 220, as will be described below, are configured to optimize the above-described trade-off by minimizing the required forces when pivoting jaw members 210, 220 is paramount and minimizing clearance when alignment of jaw members 210, 220 is paramount. That is, the required forces are minimized as jaw members 210, 220 are moved from the spaced-apart position towards the approximated position, thus facilitating approximation of jaw members 210, 220, while clearance is minimized as jaw members 210, 220 reach the approximated position, thus facilitating accurate alignment of jaw members 210, 220 when approximated about tissue.

With continued reference to FIGS. 4-7, in conjunction with FIGS. 2A-2B, and to FIG. 6 in particular, head portion 254 of pin 252 defines an inwardly-facing annular surface 282 including first and second semi-circumferentially ramped segments 283a, 283b. Ramped segments 283a, 283b are connected to one another at each end thereof to form the annular configuration of surface 282. More specifically, semi-circumferentially ramped segments 283a, 283b are circumferentially sloped in similar directions and are interconnected by first and second steps 284a, 284b, respectively. Surface 282 may further be radially sloped such that surface 282 defines an inclined configuration in a radially-outward direction.

Figure 7:
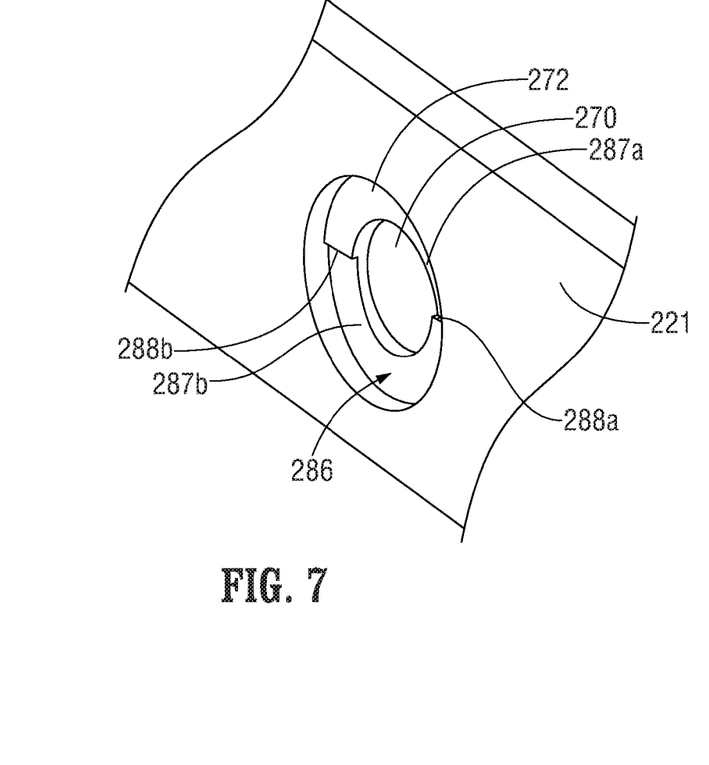
FIG. 7 is a side, perspective view of an aperture of the pivot having a complementary surface corresponding with the pin of FIG. 6.

Referring still to FIGS. 4-7, in conjunction with FIGS. 2A-2B, and to FIG. 7 in particular, shoulder 272 of aperture 270 of proximal flange 221 of jaw member 220 defines an outwardly-facing annular surface 286 shaped complementary to surface 282 of pin 252 (see FIG. 6). More specifically, surface 286 of shoulder 272 defines first and second semi-circumferentially ramped segments 287a, 287b that are interconnected by first and second steps 288a, 288a, respectively. Surface 286 may further be radially sloped such that surface 282 defines a declined configuration in a radially-outward direction.

Continuing with reference to FIGS. 4-7, in conjunction with FIGS. 2A-2B, when end effector assembly 200 is fully assembled, surface 286 of shoulder 272 of aperture 270 is disposed in slidably contact with surface 282 of pin 252. Thus, when jaw members 210, 220 are pivoted between the spaced-apart and approximated positions, surfaces 282, 286 are slid along one another. In the spaced-apart position of jaw members 210, 220, segment 283a of surface 282 opposes and abuts segment 287a of surface 286, while segment 283b of surface 282 opposes and abuts segment 287b of surface 286. In this position, step 284a defined on surface 282 and step 288a defined on surface 286 are disposed in close proximity to one another, while step 284b defined on surface 282 and step 288b defined on surface 286 are disposed in close proximity to one another. Thus, the most-inclined ends of segments 283a, 283b of surface 282 are positioned adjacent the most-declined ends of segments 287a, 287b of surface 286, and vice versa. As a result of this configuration, maximum clearance between proximal flanges 211, 221 of jaw members 210, 220, respectively, are provided, thus minimizing the frictional forces and thereby reducing the force required to pivot jaw members 210, 220 from the spaced-apart position towards the approximated position. Although relative lateral movement or tilting between jaw members 210, 220 may occur in this maximum-clearance state, such occurrences are not detrimental since misalignment is only a concern when grasping, treating, and/or cutting tissue, e.g., when jaw members 210, 220 are disposed in the approximated position.

As jaw members 210, 220 are pivoted towards the approximated position, and, thus, as surfaces 282, 286 are rotated along and relative to one another, segments 283a, 287b are moved toward opposition and abutment with one another and, likewise, segments 283b, 287a are moved towards opposition and abutment with one another. That is, as jaw members 210, 220 approach the approximated position, step 284a defined on surface 282 and step 288b defined on surface 286 are moved into close proximity, while step 284b defined on surface 282 and step 288a defined on surface 386 are moved into close proximity. In this configuration, the most-inclined ends of segments 283a, 283b of surface 282 are positioned adjacent the most-inclined ends of segments 287a, 287b of surface 286. Thus, minimum-clearance or a relatively tight-fit engagement is established. Alignment in this minimum-clearance state is facilitated by the complementary radially sloped configurations of surfaces 282, 286 of pin 252 and shoulder 272, respectively. Lateral movement or tilting of jaw members 210, 220 relative to one another is also inhibited due to the minimum-clearance in this minimum-clearance state, thus maintaining accurate alignment of jaw members 210, 220 when disposed in the approximated position. Although the forces required to close jaw members 210, 220 beyond the approximated position are relatively high in this minimum-clearance state, such is not a concern, as the approximated position is a static state and jaw members 210, 220 need not be closed beyond the approximated position.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector assembly for a surgical device, the end effector assembly comprising:
   first and second jaw members pivotable relative to one another between a spaced-apart position and an approximated position for grasping tissue therebetween, the first and second jaw members including first and second proximal flanges, respectively; and
   a pivot pin coupling the proximal flanges of the jaw members to one another to permit pivoting of the jaw members between the spaced-apart and approximated positions, the pivot pin including a body and a head, the body coupled to the first proximal flange, the head defining a first ramped surface configured to directly contact a second ramped surface of the second proximal flange, the first ramped surface configured to slide along the second ramped surface, the first ramped surface having a size substantially the same as a size of the second ramped surface,
   wherein, in the spaced-apart position of the jaw members, the first and second ramped surfaces are oppositely disposed such that a maximum clearance is defined between the first and second proximal flanges, and
   wherein, in the approximated position of the jaw members, the first and second ramped surfaces are similarly disposed such that a minimum clearance is defined between the first and second proximal flanges,
   wherein the first ramped surface includes first and second ramped segments interconnected by first and second steps, and wherein the second ramped surface includes third and fourth ramped segments interconnected by third and fourth steps, the first step configured to contact the third step and the second step configured to contact the fourth step.

2. The end effector assembly according to claim 1, wherein, in the spaced-apart position of the jaw members, the first and third ramped segments are disposed adjacent one another, the second and fourth ramped segments are disposed adjacent one another, the first and third steps are disposed adjacent one another, and the second and fourth steps are disposed adjacent one another.

3. The end effector assembly according to claim 1, wherein, in the approximated position of the jaw members, the first and fourth ramped segments are disposed adjacent one another, the second and third ramped segments are disposed adjacent one another, the first and fourth steps are disposed adjacent one another, and the second and third steps are disposed adjacent one another.

4. The end effector assembly according to claim 1, wherein the first and second ramped surfaces are radially sloped in similar directions.

5. The end effector assembly according to claim 1, wherein a portion of the body of the pivot pin is fixedly engaged within an aperture defined through the first proximal flange.

6. The end effector assembly according to claim 1, wherein each jaw member further includes a distal jaw portion, the distal jaw portions defining tissue-contacting surfaces configured to grasp tissue therebetween upon movement of the jaw members to the approximated position.

7. The end effector assembly according to claim 6, wherein at least one of the jaw members is adapted to connect to a source of energy for conducting energy between the tissue-contacting surfaces and through tissue grasped therebetween to treat tissue.

8. The end effector assembly according to claim 1, wherein, when the maximum clearance is defined between the proximal flanges, at least some degree of lateral movement and tilting of the jaw members relative to one another is permitted, and wherein, when the minimum clearance is defined between the proximal flanges, the jaw members are maintained in alignment with one another.

9. The end effector assembly according to claim 1, wherein an extending distance of the first ramped segment is substantially the same as an extending distance of the third ramped segment, and wherein an extending distance of the second ramped segment is substantially the same as an extending distance of the fourth ramped segment.

10. An end effector assembly for a surgical device, the end effector assembly comprising:
- a first jaw member including a first proximal flange portion and a first distal jaw portion, the first proximal flange portion defining a first aperture extending therethrough;
- a second jaw member including a second proximal flange portion and a second distal jaw portion, the second proximal flange portion defining a second aperture and having a shoulder disposed about the second aperture, the shoulder defining a first ramped surface; and
- a pivot pin including a body and a head, the body extending through the second aperture and engaged within the first aperture, the head defining a second ramped surface directly contacting the first ramped surface of the shoulder, the first ramped surface configured to slide along the second ramped surface, the first ramped surface having a size substantially the same as a size of the second ramped surface, the second proximal flange retained about the body between the first proximal flange and the head, and pivotable about the body and relative to the first proximal flange for moving the jaw members between a spaced-apart position and an approximated position,
- wherein, the first and second ramped surfaces are configured such that, in the spaced-apart position of the jaw members, a maximum clearance is defined between the first and second proximal flanges, and such that, in the approximated position of the jaw members, a minimum clearance is defined between the first and second proximal flanges,
- wherein the first ramped surface includes first and second ramped segments interconnected by first and second steps, and wherein the second ramped surface includes third and fourth ramped segments interconnected by third and fourth steps, the first step configured to contact the third step and the second step configured to contact the fourth step.

11. The end effector assembly according to claim 10, wherein, in the spaced-apart position of the jaw members, the first and second ramped surfaces are oppositely disposed to define the maximum clearance.

12. The end effector assembly according to claim 10, wherein, in the approximated position of the jaw members, the first and second ramped surfaces are similarly disposed to define the minimum clearance.

13. The end effector assembly according to claim 10, wherein, when the maximum clearance is defined between the proximal flanges, at least some degree of lateral movement and tilting of the jaw members relative to one another is permitted, and wherein, when the minimum clearance is defined between the proximal flanges, the jaw members are maintained in alignment with one another.

14. The end effector assembly according to claim 10, wherein, in the spaced-apart position of the jaw members, the first and third ramped segments are disposed adjacent one another, the second and fourth ramped segments are disposed adjacent one another, the first and third steps are disposed adjacent one another, and the second and fourth steps are disposed adjacent one another.

15. The end effector assembly according to claim 10, wherein, in the approximated position of the jaw members, the first and fourth ramped segments are disposed adjacent one another, the second and third ramped segments are disposed adjacent one another, the first and fourth steps are disposed adjacent one another, and the second and third steps are disposed adjacent one another.

16. The end effector assembly according to claim 10, wherein the first and second ramped surfaces are radially sloped in similar directions.

17. The end effector assembly according to claim 10, wherein the body of the pivot pin is laser welded within the aperture of the first proximal flange.

18. The end effector assembly according to claim 10, wherein each of the distal jaw portions defines a tissue-contacting surface, at least one of the tissue-contacting surfaces adapted to connect to a source of energy for conducting energy between the tissue-contacting surfaces and through tissue to treat tissue.

19. The end effector assembly according to claim 9, wherein extending distances of each of the first, second, third and fourth ramped segments are substantially the same.

20. A pivot assembly, comprising:
- a pivot pin including a body and a head, the head defining a first ramped surface including first and second ramped segments respectively interconnected by first and second steps, the pivot pin configured to facilitate movement of the first and second jaw members relative to one another between a spaced-apart position and an approximated position for grasping tissue therebetween; and
- a flange including a second ramped surface directly contacting the first ramped surface, the second ramped surface including respective third and fourth ramped segments interconnected by third and fourth steps, the first step configured to contact the third step and the second step configured to contact the fourth step,
- wherein extending distances of each of the first, second, third and fourth ramped segments are substantially the same, wherein the first and third ramped segments are configured to slide along each other, and wherein the second and fourth ramped segments are configured to slide along each other,
- wherein, in the spaced-apart position of the jaw members, the first and second ramped surfaces are oppositely disposed to define a first distance between the first and second jaw members, and
- wherein, in the approximated position of the jaw members, the first and second ramped surfaces are similarly disposed to define a second distance between the first and second jaw members.

* * * * *